(12) United States Patent
Baker et al.

(10) Patent No.: US 7,858,380 B2
(45) Date of Patent: Dec. 28, 2010

(54) SOL-GEL ENCAPSULATED HEXANUCLEAR CLUSTERS FOR OXYGEN SENSING BY OPTICAL TECHNIQUES

(75) Inventors: Gregory L Baker, Haslett, MI (US); Ruby N Ghosh, Okemos, MI (US); D J Osborn, III, Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 1253 days.

(21) Appl. No.: 11/340,207

(22) Filed: Jan. 26, 2006

(65) Prior Publication Data
US 2006/0172431 A1    Aug. 3, 2006

Related U.S. Application Data

(60) Provisional application No. 60/648,367, filed on Jan. 28, 2005.

(51) Int. Cl.
*G01N 33/22* (2006.01)
*G01M 15/00* (2006.01)
*B01F 3/04* (2006.01)
*G01N 33/00* (2006.01)
*G01N 17/00* (2006.01)

(52) U.S. Cl. .......... 436/127; 73/114.73; 250/459.1; 356/41; 436/136; 516/13; 422/91

(58) Field of Classification Search .............. 436/127
See application file for complete search history.

(56) References Cited

U.S. PATENT DOCUMENTS

| | | | |
|---|---|---|---|
| 4,453,019 A * | 6/1984 | Chang | 568/454 |
| 4,578,310 A | 3/1986 | Hatfield | |
| 4,994,396 A | 2/1991 | Lefkowitz et al. | |
| 5,173,432 A | 12/1992 | Lefkowitz et al. | |
| 5,804,161 A * | 9/1998 | Long et al. | 424/9.42 |
| 6,251,342 B1 | 6/2001 | Narula et al. | |
| 6,800,724 B2 | 10/2004 | Zha et al. | |

OTHER PUBLICATIONS

Carmichael et al., "Complexes of octa u3-chlorohexamolybdenum(II) chloride with nitrogen donors", Journal of inorganic Nuclear Chemistry, vol. 29, pp. 1535-1538 (1967).*
Amao, Fundamental Review "Proves and Polymers for Optical Sensing of Oxygen", Microchimica Acta, 143, pp. 1-12, (Aug. 2003).
Ghosh et al., "Fiber-optic oxygen sensor using molybdenum chloride cluster luminescence", Applied Physics Letters, vol. 75, No. 19, pp. 2885-2887, Nov. 8, 1999.
Jackson et al., "Efficient Singlet Oxygen Generation from Polymers Derivatized with Hexanuclear Molybdenum Clusters", American Chemical Society, vol. 8, pp. 558-564, (Jan. 1996).
MacCraith et al., "Enhanced Fluorescence Sensing Using Sol-Gel Materials", Journal of Fluorescence, vol. 12. Nos. 314, pp. 333-342, Dec. 2002.
MacCraith et al., "Fibre Optic Oxygen Sensor Based on Fluorescence Quenchnig of Evanescent-wave Excited Ruthenium Complexes in Sol-Gel Derived Porous Coatings", Analyst, .vol. 118, pp. 385-388, Apr. 1993.
Newsham et al., "Luminescent Oxide Gels", Materials Research Society, vol. 121, pp. 627-630, 1968.
Remillard et al., "Demonstration of a high-temperature fiber-optic gas sensor made with a sol-gel process to incorporate a fluorescent indicator", Applied Optics, vol. 38, No. 25, pp. 5306-5309, Sep. 1, 1999.
Sanchez et al., "Optical Properties of Functional Hybrid Organic-Inorganic Nanocomposites**", Adv. Mater. vol. 15, No. 23, pp. 1969-1994, Dec. 3, 2003.
Sheldon, "Chloromolybdenum(II) Compounds", J. Chem. Soc. pp. 1007-1014, 1960.
Sheldon, "Polynuclear Complexes of Molybdenum(II)", Nature, Vol. 184, pp. 1210-1230, Oct. 17, 1959.
Web Article: "Automatic Soxhlet Extraction", http://www.cyberlipid.org/extract/extr0010.htm, pp. 1-2, Jul. 2, 2004.
Web Article: by Jean Phalippou, "Sol-Gel: A Low Temperature Process for the Materials of the New Millennium", Sol-Gel Tutorial, http://www.solgel.com/articles/June 00/phalip/introsolgel.htm, pp. 1-5, Jul. 2004.
Web Article: "FOXY Fiber Optic Oxygen Sensor Frequently Asked Questions", pp. 1-7, Jun. 29, 2004.
Web Article: "Sol Gel Technology", http://www.chemat.com/html, pp. 1-2, Jul. 2, 2004.
Wolfbeis, "Fiber-Optic Chemical Sensors and Biosensors", Analytical Chemistry, vol. 72, No. 12, pp. 81R-89R, Jun. 15, 2000.

* cited by examiner

*Primary Examiner*—Krishnan S Menon
*Assistant Examiner*—Dirk Bass
(74) *Attorney, Agent, or Firm*—Harness, Dickey & Pierce, P.L.C.

(57) ABSTRACT

A light modifying ceramic composition comprises an oxygen permeable sol-gel matrix and a lumophore held on the matrix. In particular, the lumophore of the invention is a hexanuclear molybdenum/tungsten core having 12 anionic ligands and two ligands that are uncharged. Uncharged ligands include organic nitriles, organic phosphines, and organic arsines. In one embodiment, the ceramic composition containing the lumophore and the sol-gel matrix is applied to the end of an optical fiber to provide a remote oxygen sensor. The sensors are useful for in situ biological monitoring of oxygen either in vivo or in vitro, and in time dependent control of combustion processes such as an automobile or power plant.

36 Claims, No Drawings

SOL-GEL ENCAPSULATED HEXANUCLEAR CLUSTERS FOR OXYGEN SENSING BY OPTICAL TECHNIQUES

CROSS-REFERENCE TO RELATED APPLICATIONS

This application claims the benefit of U.S. Provisional Application Ser. No. 60/648,367, filed on Jan. 28, 2005. The disclosure of the above application is incorporated herein by reference.

INTRODUCTION

The invention relates to encapsulated luminescent clusters for oxygen sensing. In particular, a sol gel is formed in the presence of a lumophore to make a sensor to measure oxygen by luminescence quenching.

The ability to make in situ measurements of oxygen concentration is important in many technological areas, for example in medical applications and in the control of combustion of fuels in internal combustion engines, turbines, or furnaces. A number of oxygen sensors are based on the quenching by oxygen of the luminescent properties of organic, inorganic, and organometallic compounds. Fiber optic sensors offer several advantages over electrochemical as well as other designs. For example, fiber based sensors are small and flexible, and are able to probe remote locations under harsh conditions.

To work under harsh conditions, such as a chemically corrosive or high temperature environment, a fiber optic oxygen sensor must immobilize a thermally and chemically stable lumophore in a thermally and chemically stable porous matrix. Some commercially available fiber based oxygen sensors are useful only at temperatures below about 100° C. due to degradation of the lumophore at high temperatures. Sensitivity of the optical properties of these lumophores to environmental conditions, such as pH and salinity, render them unsuitable for biological and certain chemical applications. In addition, due to problems with photo-bleaching, these lumophores can not be used for continuous or time dependent monitoring of oxygen.

Derivatives of $Mo_6Cl_{12}$ as a lumophore have been found to be stable in air up to about 300° C. The excited states of these compounds tend to exhibit relatively long lifetimes and have large Stokes shifts, which simplifies high temperature operation. Since the photophysics of interest is due to electronic transitions confined to the core of the cluster, external environmental factors typically do not adversely affect the luminescent properties of these compounds.

A key challenge in designing a fiber optic based oxygen sensor is integrating a lumophore with the fiber geometry. Usually dispersed in a polymer matrix at the tip of a fiber, the polymer/lumophore composite must have a high oxygen permeability and adhere to the tip of a fiber. A number of organic polymers has been suggested for use in fiber optic based oxygen sensors. For example, Ghosh et al., in *Applied Physics Letters* 1999, Vol. 75, pg. 2885, demonstrate immobilization of $Mo_6Cl_{12}$ in a matrix of poly(trimethylsilyl-1-propyne). Other organic matrices are disclosed in Lutzkowitz et al., U.S. Pat. Nos. 4,994,396 and 5,173,432. However, the inherent temperature range of a sensor with an organic polymer is limited since the polymers cannot survive extended exposure to high temperatures. In addition, the use organic polymers is generally limited to chemical environments that do not swell the polymer matrix.

SUMMARY

A light modifying ceramic composition comprises an oxygen permeable sol-gel matrix and a lumophore held on the matrix. In one embodiment, the ceramic composition containing the lumophore and the sol-gel matrix is applied to the end of an optical fiber to provide a remote oxygen sensor. In particular, the lumophore of the invention is a hexanuclear molybdenum/tungsten core having 12 anionic ligands and two ligands that are uncharged. Non-limiting examples of uncharged ligands include organic nitrites, organic phosphines, and organic arsines. In various embodiments, the light modifying ceramic compositions exhibit luminescence and oxygen quenching after cycling in air of temperatures up to 200° C. and higher. The sensors are useful for in situ biological monitoring of oxygen either in vivo or in vitro, and in time dependent control of combustion processes such as an automobile or power plant.

DETAILED DESCRIPTION

The headings (such as "Introduction" and "Summary,") used herein are intended only for general organization of topics within the disclosure of the invention, and are not intended to limit the disclosure of the invention or any aspect thereof. In particular, subject matter disclosed in the "Introduction" may include aspects of technology within the scope of the invention, and may not constitute a recitation of prior art. Subject matter disclosed in the "Summary" is not an exhaustive or complete disclosure of the entire scope of the invention or any embodiments thereof.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations of the stated features. Specific Examples are provided for illustrative purposes of how to make, use and practice the compositions and methods of this invention and, unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the word "include," and its variants, is intended to be non-limiting, such that recitation of items in a list is not to the exclusion of other like items that may also be useful in the materials, compositions, devices, and methods of this invention.

In one embodiment, the invention provides a light modifying ceramic composition containing an oxygen permeable matrix and a lumophore held on the matrix. The matrix comprises a 3-D network of O—M—O bonds where M is a metal or metals such as silicon, zirconium, titanium, germanium, or aluminum, and O represents oxygen. The lumophore composition is represented by the structure $(Mo_nW_{6-n}X_8)Y_4L_2$. In the formula, n is $\geq 0$ and $\leq 6$, and each X and Y is independently a monoanionic ligand. In addition, each L is independently an uncharged ligand containing a group 15 element selected from group consisting of nitrogen, phosphorous, and arsenic. The Y and L are ligands bound to an $Mo_nW_{6-n}X_8$ core and each ligand L is bound to the core through the group 15 element, i.e. through nitrogen, phosphorous, or arsenic. In preferred embodiments, the ligand L is selected from the group consisting of organic nitrites, organic phosphines, and organic arsines.

In another embodiment, the invention provides a sensor adapted to determine oxygen. The sensor contains the light modifying composition described above and a wave guide adapted to transmit light to and collect light from the light modifying composition. In various embodiments, the wave guide is directly attached to the light modifying composition. For example, the wave guide can be an optical fiber or a planar wave guide.

In another embodiment, the invention provides a method of determining the concentration of oxygen in media. The method involves placing a light modifying composition such as described above into the media. Light is then transmitted to and collected from the light modifying composition and the intensity of luminescence collected from the ceramic composition is measured. The measured intensity of luminescence is compared to the intensity in the absence of oxygen to determine the concentration of oxygen in the media.

The media in which the concentration of oxygen is detected by the method can be a gas or liquid. In non-limiting embodiments, the media is a gas stream flowing over an airfoil, an animal body fluid or tissue, a body of water used for aquaculture, the exhaust stream of an internal combustion engine, a turbine, or the combustion chamber of a furnace.

In another embodiment, the invention provides a method of making a light modifying ceramic composition by a sol-gel process. To make the light modifying ceramic compositions, a sol-gel is formed in the presence of a lumophore. A lumophore described above is combined with a metal alkoxide composition comprising a metal alkoxide compound or mixture of alkoxide compounds having the general formula $R^1_m M(OR)_{V-m}$ where M is a metal of valence V, m is an integer from 0 to V−2, V−m≧2, $R^1$ is an alkyl or aryl group containing from 1 to 20 carbon atoms, and R is an alkyl group of 1 to 8 carbons. For best formation of a sol-gel, it is preferred that at least part of the metal alkoxide composition be a compound or compounds with V−m>2.

Water (preferably $H_2O$) is then added to the combination to form a reaction mixture. The pH is adjusted to an acidic pH by addition of a Lewis or Bronsted-Lowry acid. The mixture is then reacted until a 3D network comprising O—M—O bonds is formed.

Water is added at least at a trace amount. If desired, more water can be added to achieve a faster reaction to form the sol-gel. A convenient acid for adjusting the pH to an acidic level is hydrogen chloride (HCl). The acid catalyzes a hydrolysis of the M—OR groups to form M—OM—OH. Subsequent condensation of the M—OH groups forms the sol-gel matrix comprising a network of O—M—O bonds. Water and ROH formed during the sol-gel reaction are removed by heating. In a preferred embodiment, water is provided as part of the acid solution used for adjusting the pH.

Hexanuclear cores containing molybdenum and/or tungsten and their role in fluorescence quenching by oxygen are described for example in Lutzkowitz U.S. Pat. Nos. 4,994,396 and 5,173,432, the disclosures of which are incorporated by reference. In one aspect, the current invention is based in part on the observation that in an inorganic matrix such as a sol-gel, and in particular a silica sol-gel, a certain class of ligands L on the hexanuclear core leads to stable complexes suitable for measuring fluorescence or luminescence and its quenching by oxygen. Accordingly, in various embodiments, the lumophores of the invention are based on complexes of uncharged ligands L on hexanuclear molybdenum/tungsten cores. In preferred embodiments, the uncharged ligands L include groups that are not protonated under the acidic conditions of the sol-gel process, described later below. Examples include organic nitriles, organic phosphines, and organic arsines.

The invention provides a composition containing a lumophore held on a sol-gel matrix. The lumophores are represented by the structure $(Mo_nW_{6-n}X_8)Y_4L_2$ wherein n ranges from 0 ($W_6$) to 6 ($Mo_6$) and X and Y are independently a monoanionic ligand. Non-limiting examples of monoanionic ligands include halides, such as F, Cl, Br, and I; CN; SCN; OR, SR, and SeR wherein R is hydrogen, alkylaryl, or cycloalkyl; anionic nitrogen donating groups such as $NR_2$; and oxygen donating groups such as $O_2CR$, $OP(OR)_2$, $OPO(OR)_2$, borates, silicates, sulfates, and halates, wherein R is as defined above. In various embodiments, X and Y are independently selected from the halides, especially chlorine and bromine.

Chemically, the lumophore can be thought of as a core of $Mo_nW_{6-n}X_8$ onto which ligands Y and L are bound. As noted above, the ligands Y are monoanionic ligands. In preferred embodiments, the ligands Y are independently selected from halogens such as chloride and bromide.

Ligand L is an uncharged ligand containing a group 15 element selected from the group consisting of nitrogen, phosphorous, and arsenic. The ligand L is bonded onto the core through the group 15 element. In various embodiments, the ligand L has a single group 15 element that bonds to the core. In various embodiments, the ligand L is selected from organic nitriles, organic amides, organic cyanates, organic thiocyanates, organic phosphines, and organic arsines. Non-limiting examples of organic nitriles include those represented by the structure $R^3$—CN wherein $R^3$ is an alkyl group of 1 to 8 carbon atoms or an aryl group of 6 to 10 carbons optionally substituted with one or more lower alkyl groups of 1 to 4 carbons. Examples of organic phosphines include those represented by the structure $PR^4_3$, wherein $R^4$ are independently selected from hydrogen and an alkyl or aryl group containing from 1 to 10 carbon atoms. The substituents can be the same or different; preferably not all of the constituents are hydrogen. A non-limiting example is triphenylphosphine. Organic arsines include those represented by the structure $As—R^5_3$, wherein the $R^5$ groups can be the same or different and are independently hydrogen or an alkyl or aryl group of 1 to 10 carbons.

The lumophores can be synthesized by dissolving a hexanuclear cluster $(Mo_nW_{6-n})X_8Y_4$ in a solvent L. Here n, X, Y, and L are as defined above. In particular, the solvent L contains a nitrogen, phosphorous, or arsenic atom that is not protonated under the conditions of synthesis of the sol-gel described below. Once the cluster is dissolved in the ligand or solvent L, the solvent is removed to isolate the $L_2$ compound. Alternatively, the lumophores may be subsequently processed in solution.

In various embodiments, the light modifying compositions of the invention are made by forming a sol-gel in the presence of the lumophore. As a result, the light modifying composition comprises a lumophore held on a sol-gel matrix. The sol-gel matrix essentially comprises a 3D network of metal oxygen bonds represented by O—M—O where O is oxygen and M is metal. Preferred metals M include silicon, titanium, zirconium, germanium, and aluminum. In a preferred embodiment, M is a silicon. The metal M in the sol-gel matrix can be a single metal or a mixture of metals.

Sol-gels according to the invention can be synthesized by adding at least a trace of water to a precursor compound containing two or more OR groups bonded to a metal M, where R is lower alkyl such as $C_1$ to $C_6$ alkyl. The pH is adjusted to an acidic range, and the mixture is heated to polymerize the starting materials and form a 3D network of O—M—O bonds. The reaction conditions drive off solvent of condensation to form the 3D network.

In various embodiments, the metal alkoxide precursor compounds are represented by the general formula $R^1{}_m M(OR)_{V-m}$. Here, M is a metal that has a valence of V and m is chosen such that V−m is 2 or greater. $R^1$ is an alkyl or aryl group containing 1 to 20 carbon atoms, and R is a lower alkyl group such as an alkyl group containing 1 to 8 carbon atoms. Acidification of the reaction mixture can proceed with any acid capable of adjusting the pH to a range below 7. A preferred acid is HCl.

To make the light modifying ceramic compositions of the invention, a sol-gel is formed as described above in the presence of a lumophore comprising a ligand L on a molybdenum/tungsten hexanuclear core as described above. In one aspect, the synthesis is an in situ polymerization or formation of a 3D network of O—M—O bonds to form a sol-gel matrix on which the lumophore is held. In general, the lumophore does not react with the sol-gel reagents during the synthesis.

A wide range of metal alkoxides is useful to form the sol-gel matrices of the invention. In a preferred embodiment, when a silica sol-gel is to be formed, the alkoxide compound is selected from compounds $Si(OR)_4$ wherein R is a lower alkyl group such as one having 1 to 8 carbons. In various embodiments, tetraethylorthosilicate (TEOS) is used, wherein R is ethyl.

Synthesis of sol-gels is based on the chemistry of hydrolysis and condensation of metal and inorganic salts. In various embodiments, the synthesis involves preparation of a sol, gelation of the sol, and removal of the solvents. In various embodiments, sols are produced from inorganic (e.g. nitrates) or organic (e.g. alkoxides) precursors.

Sol-gels contain 3D crosslinked networks of O—M—O bonds in which M is a metal or mixture of metals. M is a metal capable of forming a 3D matrix under the conditions above and can be a single metal or a mixture of metals. Non-limiting examples include aluminum, antimony, barium, bismuth, boron, calcium, hafnium, indium, magnesium, neodymium, silicon, titanium, and zirconium. Preferred metals include silicon, titanium, zirconium, germanium, and aluminum. In various embodiments, heavy metals such as Bi, In, Nd, and Sb are less preferred because the sol gels formed from them tend to absorb in the ultraviolet. Sol-gel metals M that have unfavorable absorption profiles should be used in amounts that do not interfere unacceptably with excitation, luminescence, or oxygen quenching of the lumophores held on the sol-gel matrix. In addition, divalent compounds, such as those of Mg, Ba, and Ca should be used together with other trivalent, tetravalent, or pentavalent compounds. In particularly preferred embodiments, M is silicon and the sol-gel is a silica gel.

Metals M in the precursor compounds have valences V that range from 2 to 5. Each precursor capable of forming a network of O—M—O bonds has at least two alkoxy groups bonded to the central metal M. A number of alkoxides are commercially available. For example, the Sigma Aldrich catalog has an extensive list of sol-gel chemicals that can be found on their web page under sol-gel precursors. Non-limiting examples include aluminum ethoxide, aluminum isopropoxide, aluminum phenoxide, aluminum tributoxide, antimony ethoxide, antimony butoxide, antimony propoxide, barium isopropoxide, diisopropoxymethylborane, hafnium tert-butoxide, indium isopropoxide, tetrabutylorthosilicate, tetraethylorthosilicate, tetramethylorthosilicate, tetrapropylorthosilicate, diethoxydiphenylsilane, diethoxymethyloctadecylsilane, diethoxymethylphenylsilane, isobutyltrimethoxysilane, propyltriethoxysilane, triethoxyisobutylsilane, triethoxyoctylsilane, triethoxyphenylsilane, trimethoxyoctylsilane, trimethoxypropylsilane, tin (IV) tert-butoxide, titanium butoxide, titanium ethoxide, titanium isopropoxide, titanium methoxide, titanium propoxide, zirconium tert-butoxide, zirconium ethoxide, zirconium isopropoxide, and zirconium propoxide. In various embodiments, the use of heavy metal precursor compounds such as those containing Bi, In, Nd, and Sb, is minimized in order not to form a sol-gel matrix that would interfere with excitation and luminescence of the lumophores.

The photophysics and physical properties of molybdenum/tungsten hexanuclear lumophores such as described above are well suited for oxygen sensing schemes. In a sol-gel, clusters of the hexanuclear lumophores are dispersed and held on a matrix comprising O—M—O bonds as described above. Absorption of UV photons through a broad absorption band of about 300 to 400 nm raises the clusters to an excited electronic state. Emission of red luminescence from the excited state is efficiently quenched by ground state triplet oxygen. In addition, there is a large Stokes shift (for example greater than 300 nm) so that the luminescence is readily detectable by integrating over the broad emission band. In addition, well known filtering techniques can be used to separate pump and signal beams The methods of the invention are based in part on the discovery that in a sol-gel matrix, certain ligands L can be used to provide clusters of molybdenum/tungsten hexanuclear compounds that exhibit efficient luminescence and quenching by oxygen when excited in the UV. Accordingly, it has been found that lumophores containing uncharged ligands L, especially those selected from the group consisting of organic nitrites, organic phosphines, and organic arsines, are well dispersed in the sol-gel matrix and give suitable results when used to measure oxygen quenching of its luminescence.

The oxygen concentration can be directly determined from the intensity of the collected luminescence from the hexanuclear compounds after the calibration of the sensor. It is normally observed that the ratio of the luminescence intensity in the presence (I) and absence of oxygen ($I_0$) of concentration $[O_2]$ is given by the Stern-Volmer equation:

$$I/I_0 = (1 + C[O_2])^{-1}.$$

C is a constant for each cluster/matrix composite that can be experimentally determined by comparing the intensity of the collected luminescence as a function of oxygen concentration with the intensity of the luminescence observed in the absence of oxygen. Thus, oxygen concentrations from about 0.09% to 90% are readily measurable by the luminescence technique of the invention.

The concentration of oxygen in media can thus be measured by determining the quenching of luminescence of the light modifying compositions of the invention. The light modifying composition is first placed in the media. Light is then transmitted to and collected from the light modifying composition. The collected light from the light modifying composition is analyzed to determine the intensity of the luminescence. The measured intensity of the luminescence is then compared to the intensity in the absence of oxygen to determine the concentration of oxygen in the media.

Light is transmitted to the light modifying composition by a number of techniques. Non-limiting examples include optical wave guides such as optical fibers, and optics systems including lenses, mirrors, lasers, and the like.

Light is collected form the light modifying composition by suitable techniques. Non-limiting examples include optical wave guides such as optical fibers, and optical systems such as those containing lenses and mirrors. The use of optical wave guides is suited to use of the method in embodiments where the lumophore/sol-gel composition is directly attached to a sensor and inserted into the medium. The use of optical systems such as those containing lenses, mirrors, and lasers are suited to embodiments of the method wherein the luminescence is excited and/or collected remotely.

The media in which the lumophore containing light modifying composition is placed can be any media in which it is desired to measure the concentration of oxygen. In various embodiments, the media in which oxygen concentration is determined includes a body of water used for aquaculture, a gas stream flowing over an air foil, animal body fluid or tissue, or the exhaust stream of a internal combustion engine and turbines.

Measurements of oxygen partial pressure in the gas stream surrounding an aerodynamic surface such as an airfoil can be used to determine lift and other aerodynamic parameters. In a non-limiting embodiment, part of a surface or an entire surface of an airfoil is coated with the sol-gel encapsulated hexanuclear compounds of the invention. The airfoil surface is then illuminated by ultraviolet exciting light and the resulting luminescence is recorded, for example by a camera at various time intervals. In one embodiment, the degree of quenching of the luminescence is used to produce a spatial map of the oxygen partial pressure around the aerodynamic surface. The oxygen partial pressure is directly proportional to the total air pressure, so that lift forces on the aerodynamic surface can be calculated and a spatial map of the partial pressure of oxygen can be used to produce a 3D image of the lift forces on the airfoil. In a further embodiment, a series of images of the luminescence intensity around the airfoil is recorded at fixed time intervals. The technique can then be used to create a movie of the lift forces on the airfoil as conditions (for example in a wind tunnel) are varied with time. In these embodiments, the compositions containing the hexanuclear cores of the invention serve as a pressure sensitive paint. The application of pressure sensitive paints on airfoils and the like to measure oxygen pressure based on the quenching of luminescence is described for example in Gouterman et al., U.S. Pat. No. 5,965,642, the disclosure of which is incorporated by reference.

In a further non-limiting embodiment, in the field of aquaculture, such as sea water or fresh water fish farming in an enclosed area, there exists a need to monitor the oxygen concentration in the water. Oxygen concentration is one of the vital parameters that determine the rate of fish growth and success in reproduction. In one embodiment, ozonation is used to control the oxygen content within specified levels. An array of fiber optic oxygen sensors containing the hexanuclear compounds of the invention held on a sol-gel matrix are deployed in the fish tank at various depths and in different positions to monitor the oxygen content of the water. Excitation and detection optics are located at the nearer end of the optical end of the optical fiber to allow for remote sensing of the oxygen concentration in the tank. The sol-gel encapsulated hexanuclear compounds are located at the far end of the optical fiber.

In various embodiments, the fiber optic sensor described above is used in biological and health applications. For example, the sensors suited to monitor the oxygen concentration either in vivo or in vitro in biologically relevant systems such as animal body fluid or tissue, or in medical applications where for example it is desired to monitor the externally supplied oxygen to an anesthetized patient who is unable to breathe on his own. Further non-limiting examples include monitoring the health of a human heart stored in a nutrient bath awaiting transplantation into a patient, monitoring the oxygen flow to an anaesthetized patient and monitoring the oxygen concentration as a function of time in a biological experiment such as in a fermentor or a Petri dish. Both spatially resolved oxygen "maps" and temporal monitoring of oxygen can be obtained with the fiber optic oxygen sensor.

Although the invention is not to be limited by theoretical considerations, it appears the hexanuclear molybdenum or tungsten clusters described above are well suited for these applications at least in part because external factors such as salinity, pH, temperature and presence of other chemicals, such as anesthetics, are not expected to adversely affect the luminescent properties. In addition, sol-gel matrices such as silica gels are expected to be biologically compatible.

In one aspect, a reflection mode fiber optic sensor is used in these biological systems. The far end of the optical fiber is coated with the sol-gel encapsulated clusters and the near end of the optical fiber is used for excitation and detection of the luminescence. Using an array of fiber sensor imbedded in animal tissue, two dimensional or three dimensional spatial maps of the oxygen flow can be obtained. In a preferred embodiment, the active area of the sensor is miniaturized, for example to an area of 100 μm or less, by choosing an appropriate diameter for the optical fiber. The spatial resolution of the oxygen "map" is then determined by the active area of the sensor and the specific placement of each fiber sensor in the area. Single or arrays of fiber sensors can also be used to monitor oxygen concentration as a function of time. In various embodiments, the method is used for time dependent monitoring of oxygen flow in (i) a gas stream (such as the animal respiratory system) or an (ii) animal body fluid or (iii) animal tissue.

The invention has been described above with respect to preferred embodiments. Further non-limiting disclosure is provided in the examples that follow.

EXAMPLES

Glassware is oven dried prior to use. Acetonitrile (HPLC grade) is dried over calcium hydride and distilled prior to use. Tetraethylorthosilicate (TEOS, Aldrich 98%) and hydrochloric acid (electronics grade) are used as received. Molybdenum dichloride ($Mo_6Cl_{12}$, Cerac Inc) is recrystallized from 6M HCl as described in J. C. Sheldon, J. Chem. Soc. 1007 (1960). Heating the hydrochloride salt under vacuum at 150° C. for 2 hours, and then at 210° C. for 48 hours provides purified $Mo_6Cl_{12}$.

Example 1

The acetonitrile complex of $Mo_6Cl_{12}$ is prepared by placing dry purified $Mo_6Cl_{12}$ (100 mmol) into a cellulose Soxhlet extraction thimble. The Soxhlet apparatus is flushed with nitrogen. The $Mo_6Cl_{12}$ is then extracted with 250 mL of dry acetonitrile for one week. Concentration of the resulting clear yellow solution to 10 mL gives an orange/yellow solution of the acetonitrile complex (cluster concentration of about $2\times10^{-3}$M).

Example 2

The acetonitrile complex of Example 1, (1.4 mL 7 mmol) is added with stirring to TEOS (2.0 mL, 9.0 mmol) in a 10 mL Erlenmeyer flask. Water (0.65 mL, adjusted to pH 1 with HCl) is added and the solution stirred for 1 hour at room temperature. The stir bar is removed and the flask is heated in an oil bath at 70° C. for 2.5 hours. The solution is transferred to a scintillation vial, capped, and aged at room temperature until use.

Example 3

Quartz microscope slides are cut into 1.25 cm by 2.45 cm pieces. Slides are handled with gloves and tweezers to minimize surface contamination. They are washed with detergent, rinsed in distilled water, soaked in 5 M NaOH in 95% ethanol, rinsed and distilled and stored in distilled water until use. Prior to deposition of the sol-gel of Example 2 by dipping, the slides are removed from distilled water and dried under a stream of nitrogen. Slides are dipped by hand at a rate of about 1 mL/sec and placed directly into a scintillation vial. The vial is kept and stored on its side. The vial containing the sol-gel solution is capped after each dip coat in order to minimize evaporation. A first coat is applied after the solution is aged for 64.5 hours. A second and third coat, are applied 10 and 37 minutes after the first coat. After drying at room temperature in a capped vial for two weeks, the films are thermally cured in air at 70° C. for 24 hours.

Example 4

Silica fibers are cleaved and the cladding is removed to expose the inner silica core. They are then cleaned using a 1:1 mixture of concentrated sulfuric acid and 30% hydrogen peroxide (piranha solution) to remove any remaining organic polymer coating, soaked in 5 M NaOH in 95% ethanol, rinsed with distilled water for at least 1 hour, and stored in distilled water until use. The fibers are dried under a stream of house nitrogen just prior to dipping. Using a pair of tweezers, the fibers are dipped into a sol-gel solution such as that of Example 2 (viscosity approximately equal to the consistency of honey), and the fibers are suspended by their uncoated end from the inside of a vial cap. The vial is then sealed, and after two weeks of drying at room temperature, the fibers are thermally cured in air at 70° C. for 24 hours.

Example 5

Absorption and fluorescence measurements indicate that the emission line shape for the hexanuclear compound of Example 1 is the same when measured in solution or incorporated into the sol-gel matrix.

Measurements of luminescence in solution are performed by placing the solution in a quartz cuvette sealed with an airtight septum. Spectra are measured in laboratory air and high purity nitrogen. All gases are bubbled through the solution for 10 to 15 minutes at a rate of 10 mL/minute prior to obtaining spectra. Measurements of sol-gel immobilized hexanuclear compounds are made in a similar manner. The film coated side of the quartz slide is irradiated at an angle of about 40° with a 90° angle maintained between the excitation beam and the detector. The sol-gel film containing the hexanuclear compounds of the invention exhibits luminescence quenching by oxygen in a manner similar to that exhibited by the compounds in solution. Oxygen quenching of the compound luminescence is preserved after heating the sol-gel composite containing the compound to 200° C.

Comparative Example

A lumophore is made as in Example 1 and a sol-gel made as in Example 2, except that alcohol was added as a co-solvent to make a lumophore where L is an alcohol and does not contain N, P, or As. After drying at 70° C., the luminescence of the lumophore in the sol-gel is significantly poorer than that of the lumophore in solution as well as sol-gel matrices prepared without added alcohol.

Although the invention has been described above with respect to non-limiting examples, it is to be understood that the invention is not limited to the enclosed embodiments. Variations and modifications that will occur to a person of skill in the art upon reading the description are also intended to be within the scope of the invention, which is defined in the appended claims.

We claim:

1. A light modifying ceramic composition comprising:
    an oxygen permeable matrix comprising a 3-D network of O—M—O bonds, wherein O is oxygen and M is one or more metals selected from the group consisting of silicon, zirconium, titanium, germanium, and aluminum; and
    a lumophore held on the matrix, wherein the lumophore comprises a hexanuclear compound represented by the structure $$(Mo_nW_{6-n}X_8)Y_4L_2$$

wherein
    $0 \leq n \leq 6$;
    each X and Y is independently a monoanionic ligand;
    each L is independently an uncharged ligand containing a group 15 element selected from the group consisting of N, P, and As;
    Y and L are ligands bound to a $Mo_nW_{6-n}X_8$ core; and
    each ligand L is bound to the core through the group 15 element.

2. A composition according to claim 1, wherein X and Y are halogen.

3. A composition according to claim 1, wherein X and Y are chloro.

4. A composition according to claim 1, wherein X and Y are bromo.

5. A composition according to claim 1, wherein L is an organic nitrile.

6. A composition according to claim 2, wherein L is an organic nitrile.

7. A composition according to claim 1, wherein L is an organic phosphine.

8. A composition according to claim 1, wherein L is an organic arsine.

9. A composition according to claim 1, wherein L is selected from the group consisting of $CH_3CN$ and $CH_3CH_2CN$.

10. A composition according to claim 1, wherein X and Y are independently chloro or bromo, and L is $CH_3CN$.

11. A sensor adapted to determine oxygen comprising:
    a light modifying composition according to claim 1; and
    a waveguide adapted to transmit light to and collect light from the light modifying composition.

12. A sensor adapted to determine oxygen comprising:
a light modifying composition according to claim 2; and
a waveguide adapted to transmit light to and collect light from the light modifying composition.

13. A sensor adapted to determine oxygen comprising:
a light modifying composition according to claim 5; and
a waveguide adapted to transmit light to and collect light from the light modifying composition.

14. A sensor adapted to determine oxygen comprising:
a light modifying composition according to claim 6; and
a waveguide adapted to transmit light to and collect light from the light modifying composition.

15. A method of determining the concentration of oxygen in media by measuring the quenching of luminescence by oxygen of a light modifying composition, the method comprising;
    (a) placing the sensor according to claim 11 into the media;
    (b) transmitting light to and collecting light from the light modifying composition;
    (c) measuring the intensity of luminescence collected from the light modifying composition; and
    (d) comparing the measured intensity to the intensity in the absence of oxygen to determine the concentration of oxygen in the media.

16. A method according to claim 15, wherein the matrix is a sol-gel matrix.

17. A method according to claim 16, wherein the sol-gel is a silica gel.

18. A method according to claim 15, wherein X and Y are independently halogen and L is an organic nitrile.

19. A method according to claim 18, wherein L is acetonitrile.

20. A method according to claim 15, wherein X and Y are independently halogen and L is an organic phosphine.

21. A method according to claim 15, wherein X and Y are independently halogen and L is an organic arsine.

22. A method according to claim 15, wherein n>0.

23. A method according to claim 15, wherein n=6.

24. A method according to claim 15, wherein the media is a gas.

25. A method according to claim 15, wherein the media is a liquid.

26. A method according to claim 15, wherein the media is a gas stream flowing over an airfoil.

27. A method according to claim 15, wherein the media is an animal body fluid or tissue.

28. A method according to claim 15, wherein the media is a body of water used for aquaculture.

29. A method according to claim 15, wherein the media is an exhaust gas stream of an internal combustion engine or turbine.

30. A method of making a light modifying ceramic composition according to claim 1 by a sol-gel process, comprising:
    combining a luminescent dye with an alkoxide compound containing —OR groups bonded to a metal M, wherein R is alkyl of 1 to about 8 carbons;
    adding water to the combination to form a reaction mixture; and
    reacting the mixture until a 3-D network comprising O—M—O bonds is formed,
    wherein the luminescent dye comprises
    $(Mo_nW_{6-n}X_8)Y_4L_2$
    wherein
    $0 \leq n \leq 6$;
    X and Y independently monoanionic ligands;
    each L is an uncharged ligand containing a group 15 element selected from the group consisting of N, P, and As;
    Y and L are ligands bound to a $Mo_nW_{6-n}X_8$ core; and
    each ligand L is bound to the core through the group 15 element.

31. A method according to claim 30, wherein the alkoxide compound comprises $Si(OR_4)$.

32. A method according to claim 30, wherein the alkoxide compound comprises tetraethylorthosilicate (TEOS).

33. A method according to claim 30, wherein L comprises an organic nitrile.

34. A method according to claim 30, wherein L is acetonitrile.

35. A method according to claim 33, wherein the alkoxide compound is tetraethylorthosilicate (TEOS).

36. A method according to claim 35, wherein X and Y are halogen.

* * * * *

UNITED STATES PATENT AND TRADEMARK OFFICE
CERTIFICATE OF CORRECTION

PATENT NO. : 7,858,380 B2
APPLICATION NO. : 11/340207
DATED : December 28, 2010
INVENTOR(S) : Gregory L. Baker, Ruby N. Ghosh and D. J. Osborn, III It is certified that error appears in the above-identified patent and that said Letters Patent is hereby corrected as shown below:

Column 2, line 11, "nitrites" should be --nitriles--.

Column 3, line 6, "nitrites" should be --nitriles--.

Column 3, line 53, "M-OM-OH" should be --M-OH--.

Column 6, line 38, "nitrites" should be --nitriles--.

Signed and Sealed this
Thirteenth Day of September, 2011

David J. Kappos
*Director of the United States Patent and Trademark Office*